(12) United States Patent
Omura

(10) Patent No.: US 9,275,770 B2
(45) Date of Patent: Mar. 1, 2016

(54) X-RAY RADIATION GENERATION APPARATUS WITH ARM ANGLE RESTRICTION UNIT

(71) Applicant: CANON KABUSHIKI KAISHA, Tokyo (JP)

(72) Inventor: Satoru Omura, Chigasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/644,562

(22) Filed: Mar. 11, 2015

(65) Prior Publication Data
US 2015/0270022 A1 Sep. 24, 2015

(30) Foreign Application Priority Data

Mar. 20, 2014 (JP) .................................. 2014-059080
Jan. 9, 2015 (JP) .................................. 2015-003612

(51) Int. Cl.
*A61B 6/08* (2006.01)
*G21K 5/10* (2006.01)
*A61N 5/10* (2006.01)
*A61B 6/00* (2006.01)
*A61G 7/10* (2006.01)

(52) U.S. Cl.
CPC ................ *G21K 5/10* (2013.01); *A61B 6/4429* (2013.01); *A61B 6/4458* (2013.01); *A61N 5/1078* (2013.01); *A61G 7/1074* (2013.01)

(58) Field of Classification Search
CPC ......... F21V 21/30; F21V 21/14; F21V 21/22; F21V 21/28; F21V 21/26; G21K 5/10; A61N 5/1078; A61B 6/4405; A61B 6/4452
USPC .......................................... 378/193, 197, 198
See application file for complete search history.

(56) References Cited

U.S. PATENT DOCUMENTS

| | | | | |
|---|---|---|---|---|
| 3,801,790 A | * | 4/1974 | Gotzl | A61B 6/4405 378/117 |
| 4,752,948 A | * | 6/1988 | MacMahon | A61B 6/4405 378/193 |
| 5,388,142 A | * | 2/1995 | Morris | A61B 6/4405 378/196 |
| 5,680,436 A | * | 10/1997 | Nyzen | A61B 6/4464 248/316.4 |
| 5,712,482 A | * | 1/1998 | Gaiser | A61B 6/4405 250/363.08 |
| 6,754,306 B2 | | 6/2004 | Cho et al. | 378/102 |
| 7,585,109 B2 | * | 9/2009 | Denley | A61B 6/447 378/193 |
| 7,785,006 B2 | * | 8/2010 | Kim | A61B 6/4441 378/181 |
| 2003/0208844 A1 | * | 11/2003 | Moffa | A61G 7/1017 5/86.1 |
| 2006/0176695 A1 | * | 8/2006 | Gordin | H05B 41/392 362/263 |
| 2012/0195404 A1 | | 8/2012 | Omura | 378/62 |
| 2014/0098942 A1 | | 4/2014 | Omura et al. | 378/197 |
| 2014/0233703 A1 | | 8/2014 | Omura et al. | 378/98 |
| 2015/0246450 A1 | * | 9/2015 | Yoneda | B25J 9/101 744/490.5 |

* cited by examiner

*Primary Examiner* — Brooke Purinton
(74) *Attorney, Agent, or Firm* — Fitzpatrick, Cella, Harper & Scinto

(57) ABSTRACT

A radiation generation apparatus includes a radiation generator which generates radiation, an arm which supports the radiation generator, and a column which supports the arm. The arm can open and close with respect to the column. The radiation generation apparatus includes a restriction unit which restricts the opening and closing angle of the arm with respect to the column in accordance with the length of the arm.

19 Claims, 10 Drawing Sheets

FIG. 4A-A
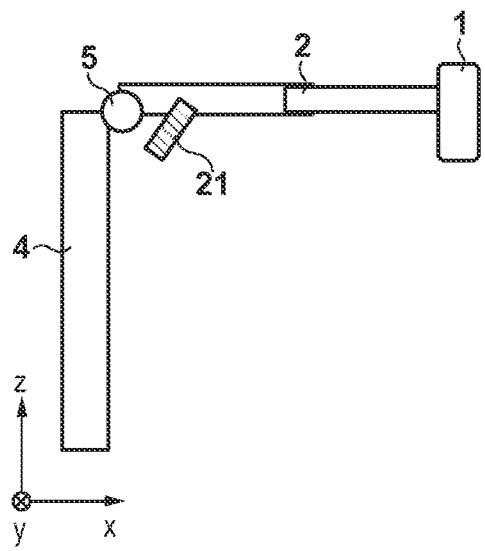
FIG. 4A-B
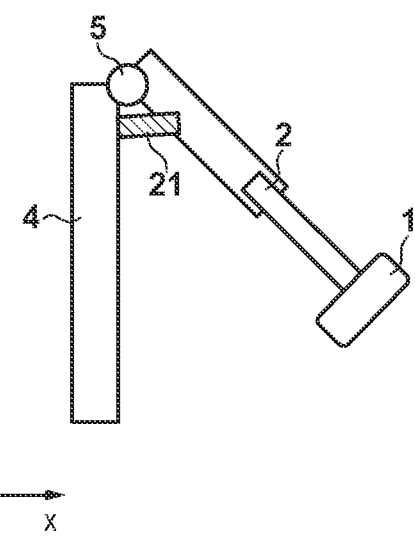
FIG. 4B-A
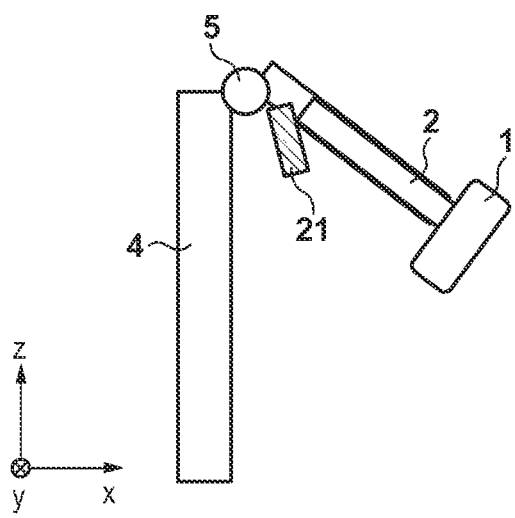
FIG. 4B-B
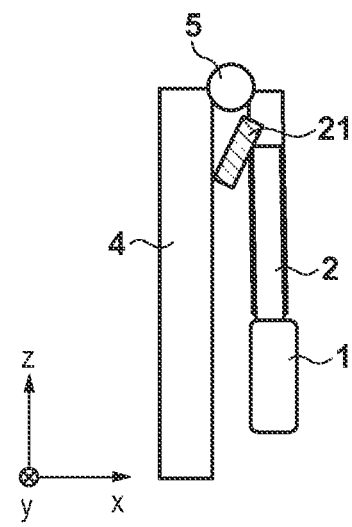

X-RAY RADIATION GENERATION APPARATUS WITH ARM ANGLE RESTRICTION UNIT

BACKGROUND OF THE INVENTION

1. Field of the Invention

The present invention relates to a radiation generation apparatus.

2. Description of the Related Art

Recently, a radiation generation apparatus which has a radiation generator mounted on a moving mechanism and is movable has been widely used as a radiation generation apparatus for home medical care and health care. The radiation generation apparatus has two kinds of arrangements, namely an arrangement for image capturing by generating radiation from the radiation generator and an arrangement for movement using the moving mechanism.

When performing radiography, for example, it is necessary to use a supporting mechanism for supporting the radiation generator at a sufficiently high position so as to capture an image of an object lying on the bed. In addition, when the extremities of an object are image capturing regions, the supporting mechanism is required to have a wide range of movement so as to hold the radiation generator and the radiation detector at proper positions regardless of the position on the bed.

U.S. Pat. No. 6,754,306 discloses an apparatus including an arm as a supporting mechanism for supporting a radiation generator, a column supporting the arm, and a supporting leg unit supporting the column and the arm, and the wheels of a moving mechanism.

According to U.S. Pat. No. 6,754,306, however, in a case in which the arm is designed to be extendable, after performing image capturing while the arm is extended longer than the column, when the operator tries to close the arm in an extended state toward the column to set the arm in a state at the time of movement, the radiation generator interferes with the ground or the supporting leg unit of the apparatus. In order to prevent such interference, it is necessary to shorten the length of the arm to a position where no interference occurs and then fold the arm. When repeatedly performing image capturing and movement, such a manipulation of the arm can impose a heavy load on the operator.

The present invention provides a radiation generation apparatus which can facilitate a manipulation of an arm without interfering with the ground (horizontal surface).

SUMMARY OF THE INVENTION

According to one aspect of the present invention, there is provided a radiation generation apparatus which includes a radiation generator configured to generate radiation, an arm configured to support the radiation generator, and a column configured to support the arm, the arm being configured to open and close with respect to the column, the apparatus comprising a restriction unit configured to restrict an opening and closing angle of the arm with respect to the column in accordance with a length of the arm.

According to another aspect of the present invention, there is provided a radiation generation apparatus which includes a radiation generator configured to generate radiation, an arm configured to support the radiation generator, and a column configured to support the arm, the arm being configured to open and close with respect to the column, the apparatus comprising a restriction unit configured to restrict an opening and closing angle of the arm with respect to the column to inhibit the arm from contacting a floor surface in accordance with a length of the arm.

Further features of the present invention will become apparent from the following description of exemplary embodiments (with reference to the attached drawings).

BRIEF DESCRIPTION OF THE DRAWINGS

FIGS. 4A-A and 4A-B are views for explaining the function of the restriction unit of the radiation generation apparatus according to the first embodiment;

FIGS. 4B-A and 4B-B are views for explaining the function of the restriction unit of the radiation generation apparatus according to the first embodiment;

DESCRIPTION OF THE EMBODIMENTS

Embodiments of the present invention will be exemplarily described in detail below with reference to the accompanying drawings. Note that the constituent elements described in the embodiments are merely examples. The technical scope of the present invention is determined by the scope of claims and is not limited by the following individual embodiments.

(First Embodiment)

Figure 1A:
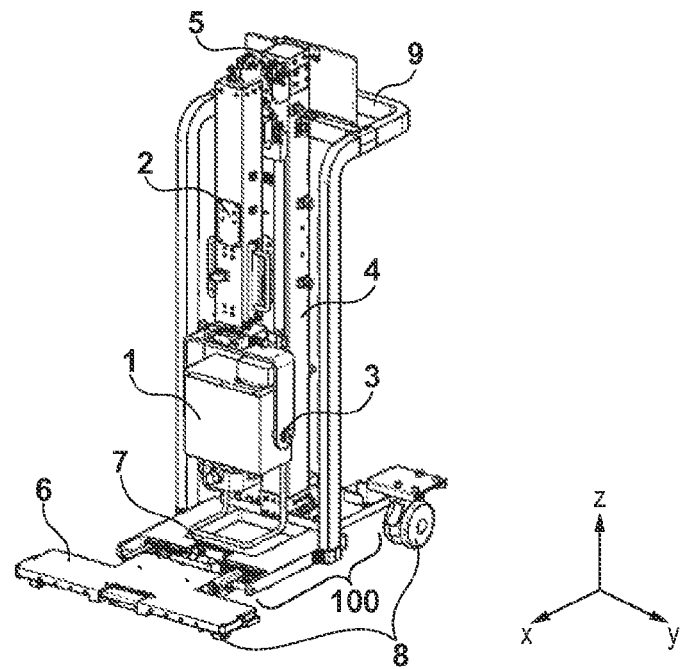
FIGS. 1A and 1B are views showing the arrangement of a radiation generation apparatus according to the first embodiment.
Figure 1B:
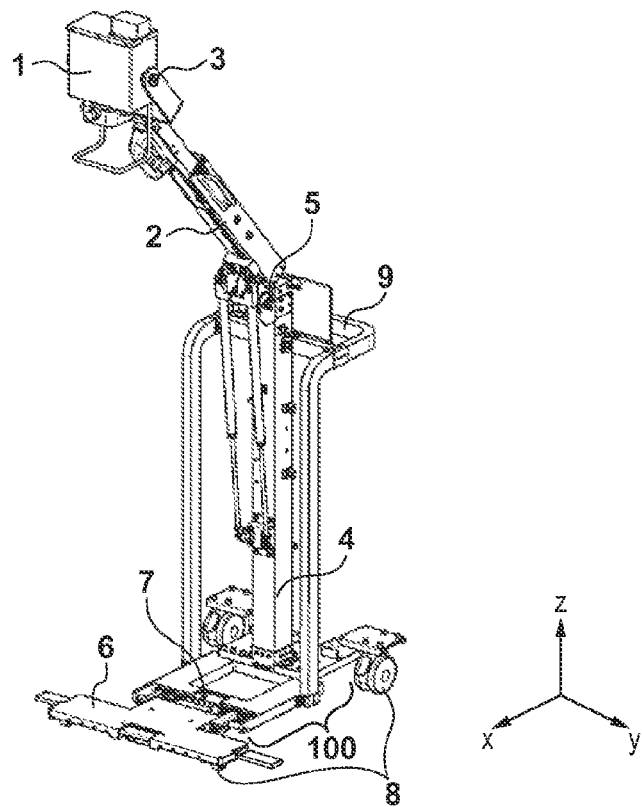

FIGS. 1A and 1B are views showing the arrangement of a radiation generation apparatus according to the first embodiment. FIG. 1A is a front perspective view of the radiation generation apparatus at the time of movement. FIG. 1B is a front perspective view of the radiation generation apparatus at the time of image capturing.

The radiation generation apparatus includes a radiation generator 1 which generates radiation, an arm 2 which supports the radiation generator 1, and a column 4 which supports the arm 2. The arm 2 can open and close with respect to the column 4. That is, the arm 2 is pivotable with respect to the column 4. The radiation generation apparatus has as its feature to have a restriction unit which restricts the opening and closing angle of the arm 2 with respect to the column 4 in accordance with the length of the arm 2. In other words, the restriction unit restricts the pivot angle of the arm 2 with respect to the column 4 in accordance with the length of the arm 2. That is, the restriction unit functions as a braking unit which brakes the arm 2 in accordance with the length of the arm 2 and the opening and closing angle of the arm 2 with respect to the column 4.

Figure 2:
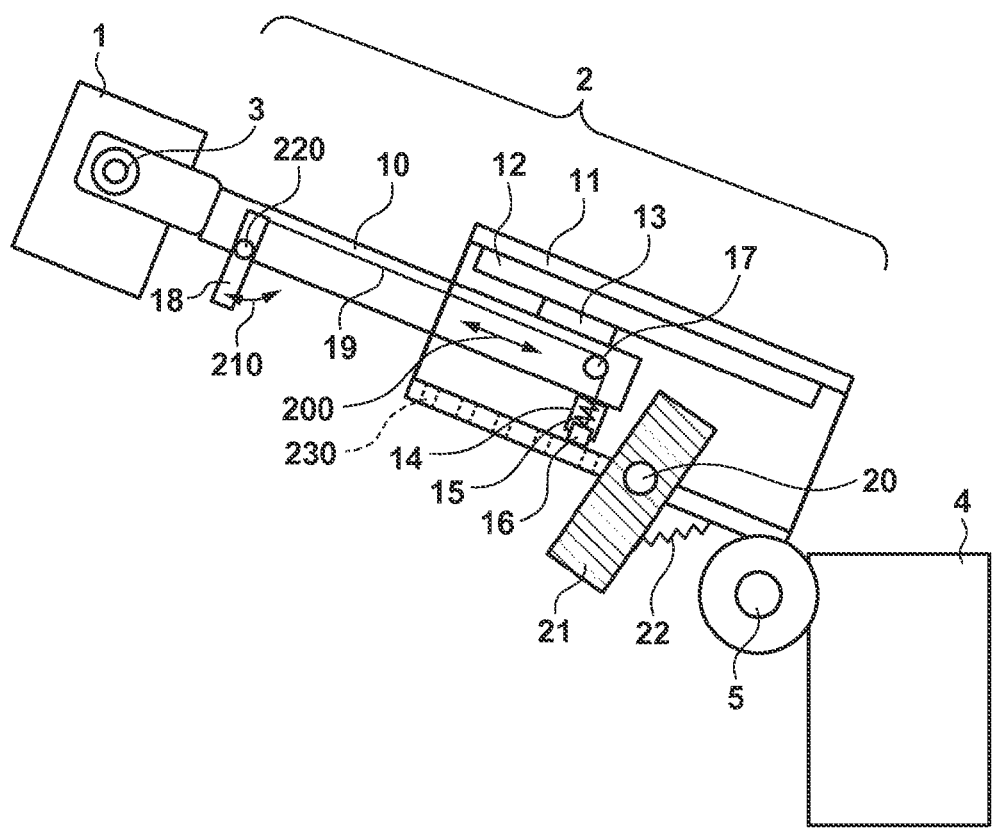
FIG. 2 is a view showing the internal structure of an arm according to the first embodiment.

FIG. 2 is a sectional view of the arm 2 when viewed from a lateral direction of the radiation generation apparatus. The arm 2 includes a fixed arm 11 supported so as to open and close with respect to the column 4 and a movable arm 10 held so as to be movable with respect to the fixed arm 11. A restriction unit 21 is supported so as to be rotatable with respect to the fixed arm 11, and restricts the opening and closing angle by changing the direction with respect to the column 4 in accordance with the movement of the movable arm 10.

A hinge unit 5 is provided between the arm 2 and the column 4. The hinge unit 5 connects the arm 2 to the column 4, and makes the arm 2 open and close with respect to the column 4. While the radiation generation apparatus is moving, the arm 2 is closed with respect to the column 4 (FIG. 1A). While image capturing is performed, the arm 2 is open with respect to the column 4 (FIG. 1B).

The movable arm 10 is held so as to be movable between the retracted position on one end side (the hinge unit 5 side), on which the fixed arm 11 is supported, and the extended position on the other end side (the distal end side) of the fixed arm 11. A restriction unit 21 restricts the opening and closing angle by changing the direction with respect to the column 4 in accordance with the movement of the movable arm 10 from the retracted position to the extended position.

The arm 2 includes a moving unit for moving the movable arm 10 along the longitudinal direction of the arm 2 and a position holding unit which holds the position at which the arm 2 is retracted/extended. The moving unit can retract and extend the arm 2. This makes it possible to ensure a wide movable range for the radiation generator 1, thereby positioning the radiation generator 1 with respect to various types of image capturing regions.

The column 4 is perpendicular or nearly perpendicular to the ground (horizontal surface) while the apparatus stands upright.

A rotating unit 3 is formed between the radiation generator 1 and the distal end portion of the arm 2 and adjusts the rotation angle of the radiation generator 1 with respect to the arm 2. Adjusting the rotation angle using the rotating unit 3 can adjust the radiation irradiation direction of the radiation generator 1.

A supporting leg unit 6 is a member which supports the column 4. A supporting leg hinge unit 7 connects a base member 100, to which the column 4 is fixed, to the supporting leg unit 6. The supporting leg hinge unit 7 supports the supporting leg unit 6 so as to make it open and close with respect to the base member 100. Note that it is possible to integrate the supporting leg unit 6 and the base member 100 without providing the supporting leg hinge unit 7.

A moving mechanism 8 can move the radiation generation apparatus. The moving mechanism 8 can move the overall radiation generation apparatus by rotating a plurality of tires or casters mounted on the lower portion of the base member 100, to which the column 4 is fixed, and the lower portion of the supporting leg unit 6, while the tires or casters are placed on the ground (horizontal surface). When moving the radiation generation apparatus, the operator can perform a moving manipulation via a handle 9.

(Arrangement of Arm 2)

The internal arrangement of the arm 2 will be described next. As shown in FIG. 2, the arm 2 includes the movable arm 10 and the fixed arm 11. The fixed arm 11 has a hollow structure. The hollow structure incorporates a moving unit for the movable arm 10 and a holding unit for holding a movement position. One end (the right end in FIG. 2) of the movable arm 10 is connected to the moving unit. The other end (the left end in FIG. 2) of the movable arm 10 is provided with the radiation generator 1 via the rotating unit 3.

One end (the right end in FIG. 2) of the fixed arm 11 is connected to the column 4 via the hinge unit 5. As the hinge unit 5 rotates, the fixed arm 11 can open and close with respect to the column 4. The movable arm 10 is arranged on the other end (the left end in FIG. 2) of the fixed arm 11. The moving unit can move the movable arm 10 in the direction of an arrow 200.

(Moving Unit for Movable Arm 10)

Referring to FIG. 2, the arrangement of the moving unit for the movable arm 10 includes a linear guide rail 12 and a sliding unit 13. The linear guide rail 12 is fixed in the fixed arm 11. The sliding unit 13 is mounted on the outer surface of the movable arm 10 and can move on the linear guide rail 12. As the sliding unit 13 linearly moves on the linear guide rail 12, the movable arm 10 can be retracted/extended with respect to the fixed arm 11.

Note that the arrangement of the moving unit is not limited to the arrangement shown in FIG. 2, and it is possible to use any arrangement which can move the movable arm 10. For example, the linear guide rail 12 may be fixed to the outer surface of the movable arm 10, and the sliding unit 13 may be mounted in the fixed arm 11. In addition, as the arrangement of the moving unit, it is possible to use a combination of a cam follower and a guide rail and a rack-pinion in addition to the linear guide rail 12 and the sliding unit 13.

(Holding Unit for Movable Arm 10)

A holding unit for holding a movement position will be described next. A slide guide 14 has a hollow structure and is arranged on the movable arm 10. A compression spring 15 is provided in the slide guide 14. A lock member 16 is mounted on the distal end of the compression spring 15. The lock member 16 is configured to be pulled from an end portion of the slide guide 14. The lock member 16 is pressed against the inner surface of the fixed arm 11 with the elastic force of the compression spring 15.

Opening portions 230 are formed in the inner surface of the fixed arm 11 at predetermined intervals. When the lock member 16 engages with one of the opening portions 230, the position of the movable arm 10 is held (fixed). That is, the movable arm 10 is fixed to the fixed arm 11.

The movable arm 10 has a hollow structure. A pulley 17 is arranged in the movable arm 10. A lock releasing handle 18 is a manipulation unit for performing an engagement releasing manipulation for the lock member 16. A wire 19 connects the lock member 16 to the lock releasing handle 18 via the pulley 17.

The lock releasing handle 18 can rotate in the direction of an arrow 210 about a rotation fulcrum 220 on the movable arm 10. When the lock releasing handle 18 in the state shown in FIG. 2 is rotated counterclockwise, a pull force acts on the wire 19 in a lateral direction (the left direction of the arrow 200). The pulley 17 converts this pull force in the lateral direction into an upward pull force which raises the lock member 16. When the upward pull force acts on the lock member 16, the lock member 16 is disengaged from the opening portion 230. In this disengaged state, the movable arm 10 can move with respect to the fixed arm 11.

When the lock releasing handle 18 is rotated clockwise, the pull force in the lateral direction (the left direction of the arrow 200) acting on the wire 19 disappears. As a result, the lock member 16 is pressed against the inner surface of the fixed arm 11 with the elastic force of the compression spring 15 without being influenced by the pull force from the wire 19. It is possible to set the length of the arm 2 to a desired length by making adjustment to engage the lock member 16 with the opening portion 230 when the length of the arm 2 becomes suitable for image capturing, while the movable arm 10 is moved in the lateral direction (the direction of the arrow 200).

(Arrangement of Restriction Unit)

The arrangement of the restriction unit 21 which restricts the opening and closing angle of the arm 2 with respect to the column 4 in accordance with the length of the arm will be described next. One end of the restriction unit 21 is connected to the fixed arm 11 via an elastic member. The other end of the restriction unit 21 contacts the movable arm 10 located at the retracted position. As the movable arm 10 moves from the retracted position to the extended position, the restriction unit 21 rotates with the force of the elastic member to change the direction with respect to the column 4 and restrict the opening and closing angle. In other words, the restriction unit 21 is controlled in accordance with the position of the movable arm 10, that is, the length of the arm 2. The restriction unit 21 restricts the opening and closing angle of the arm 2 with respect to the column 4 in accordance with the length of the arm 2. That is, the restriction unit 21 restricts the angle in the direction to close the arm 2 with respect to the column 4 in accordance with the length of the arm. More specifically, if the length of the arm 2 is longer than a predetermined length, the restriction unit 21 restricts the opening and closing angle of the arm 2 with respect to the column 4. If the length of the arm 2 is shorter than the predetermined length, the restriction unit 21 does not restrict the opening and closing angle of the arm 2 with respect to the column 4. That is, the restriction on the opening and closing angle of the arm 2 is released.

Referring to FIG. 2, a shaft 20 is provided on the fixed arm 11. The restriction unit 21 is a member configured to be rotatable about the shaft 20. A tension spring 22 connects the fixed arm 11 to the restriction unit 21. The tension spring 22 applies a pull force to the restriction unit 21 to rotate it about the shaft 20. The relative angle between the fixed arm 11 and the restriction unit 21 changes in accordance with the movement of the movable arm 10. In addition, the direction of the restriction unit 21 with respect to the column 4 changes in accordance with the movement of the movable arm 10.

As shown in FIG. 2, the upper side of the restriction unit 21 extends more into the fixed arm 11 than the shaft 20. When the movable arm 10 returns from an extended state (extended position) to a retracted state (retracted position), the movable arm 10 contacts the restriction unit 21. The lower side of the restriction unit 21 extends more out of the fixed arm 11 than the shaft 20. When the arm 2 rotates in the direction to close with respect to the column 4, the restriction unit 21 contacts the column 4.

Figure 3A:
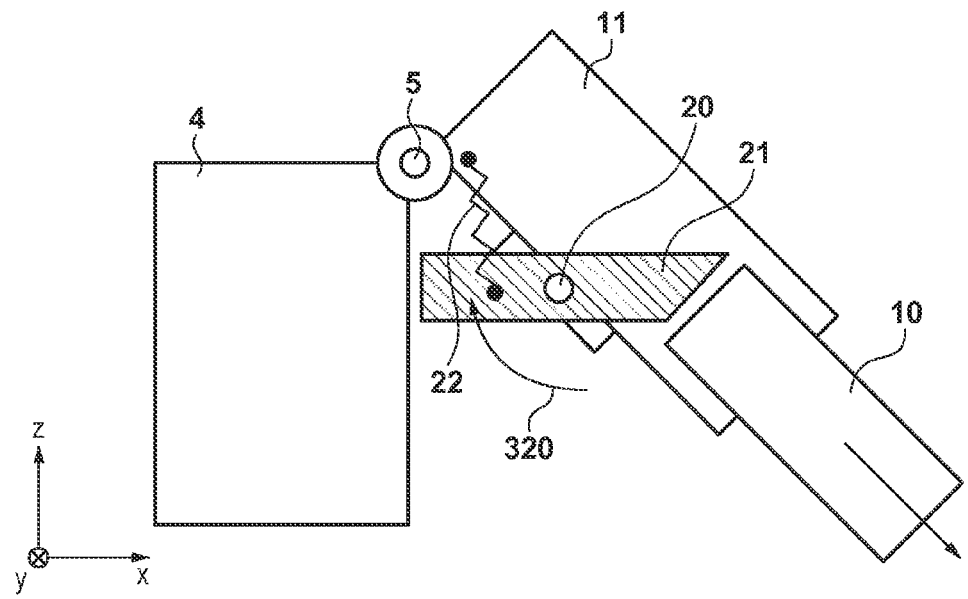
FIGS. 3A and 3B are views for explaining the operation of the restriction unit of the radiation generation apparatus according to the first embodiment.
Figure 3B:
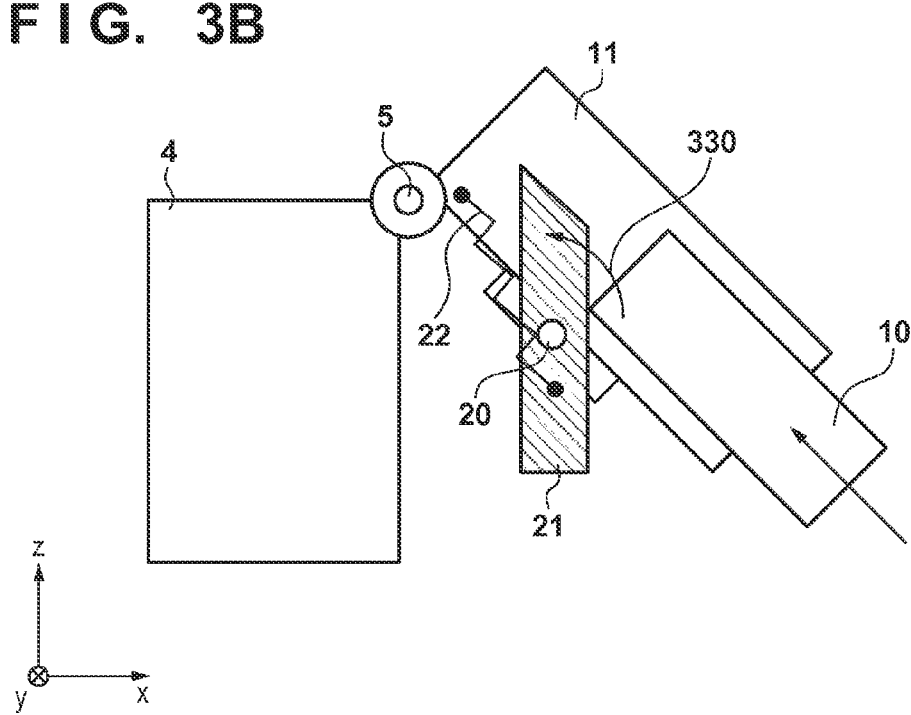

FIGS. 3A and 3B are views for explaining the operation of the restriction unit 21, and each are a sectional view of the arm 2 (the movable arm 10 and the fixed arm 11) viewed from a lateral direction of the apparatus. FIG. 3A shows a state in which the length of the arm 2 has increased (a state at an extended position). FIG. 3B shows a state in which the length of the arm 2 has decreased (a state at a retracted position).

When the arm 2 is set in an extended state (a state at an extended position), an end portion of the movable arm 10 does not contact the restriction unit 21. As a consequence, the pull force from the tension spring 22 acts on the restriction unit 21, and the restriction unit 21 rotates in the direction of an arrow 320, as shown in FIG. 3A. The distal end portion of the restriction unit 21 which extends from the fixed arm 11 is held at a position facing the column 4. The direction of the restriction unit 21 is held by the pull force of the tension spring 22 and a stopper (not shown) provided on the fixed arm 11.

When the arm 2 is set in a retracted state (a state at a retracted position), the end portion of the movable arm 10 contacts the restriction unit 21 (FIG. 3B). When the restriction unit 21 contacts the movable arm 10, a force acts on the restriction unit 21 to rotate it in the direction of an arrow 330. Although the pull force from the tension spring 22 also acts on the restriction unit 21, since the force received from the movable arm 10 is larger than the pull force, the restriction unit 21 rotates in the direction of the arrow 330 as the movable arm 10 moves.

FIGS. 4A-A, 4A-B, 4B-A, and 4B-B are views for explaining the function of the restriction unit 21. FIGS. 4A-A and 4A-B correspond to the state of the arm 2 shown in FIG. 3A. FIGS. 4B-A and 4B-B correspond to the state of the arm 2 shown in FIG. 3B. When the arm 2 moves in the direction to close with respect to the column 4 while the movable arm 10 has moved to the extended position, the restriction unit 21 contacts the column 4 to restrict the opening and closing angle of the arm 2 with respect to the column 4, and the radiation generator 1 is held at a position where it does not contact the ground (horizontal surface).

When changing the state of the arm 2, which has moved to a retracted position, from the open state shown in FIG. 4A-A to the closed state shown in FIG. 4A-B, since the restriction unit 21 contacts the column 4, the arm 2 cannot be fully closed with respect to the column 4. The restriction unit 21 restricts the opening and closing angle of the arm 2 with respect to the column 4.

On the other hand, as the movable arm 10 moves from the extended position to the retracted position, the restriction unit 21 releases the restriction on the opening and closing angle by returning the direction with respect to the column 4 to the direction before the rotation. When changing the state of the arm 2, which has moved to a retracted position, from the open state shown in FIG. 4B-A to the closed state shown in FIG. 4B-B, since the restriction unit 21 does not contact the column 4, the arm 2 can be fully closed with respect to the column 4. That is, when the arm 2 moves in the direction to close with respect to the column 4 while the movable arm 10 has moved to the retracted position, the arm 2 can move without receiving any restriction on the opening and closing angle by the restriction unit 21. The radiation generator 1 is held at a position where it does not contact the ground (horizontal surface).

According to the arrangement of this embodiment, even when trying to close the arm 2 with respect to the column 4 while the arm 2 is in an extended state, since the restriction unit 21 contacts the column 4, it is possible to restrict the opening and closing angle of the arm 2 with respect to the column 4. In addition, restricting the opening and closing angle can ensure a distance that prevents interference between the radiation generator 1 and the ground (horizontal surface). This makes it possible to provide a radiation generation apparatus which can reduce the load on the operator in returning the length of the arm 2 to a position where no interference occurs and then folding the arm, and can facilitate the manipulation of the arm without any interference with the ground (horizontal surface) and the supporting unit of the apparatus while ensuring a wide range of movement for the radiation generator 1.

(Second Embodiment)

This embodiment will exemplify the arrangement of a radiation generation apparatus including a fixing unit which fixes the position of an arm 2 while a restriction unit 21 is in contact with a column 4, in addition to the arrangement in which the restriction unit restricts the opening and closing angle, which has been described in the first embodiment. The fixing unit fixes the arm 2 so as to fix the movement of the arm 2 in the direction to open with respect to the column 4.

The same reference numerals as in FIGS. 5A and 5B to FIGS. 7A and 7B to be referred below denote the same components in the first embodiment, and a repetitive description of them will be omitted.

EXAMPLE 1

Figure 5A:
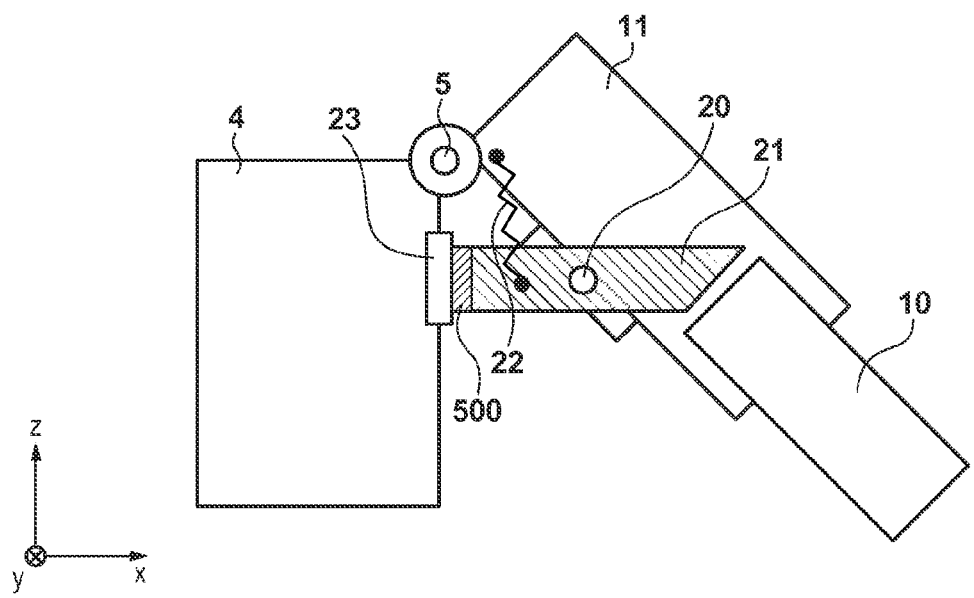
FIGS. 5A and 5B are views showing the arrangement of a radiation generation apparatus according to the second embodiment.
Figure 5B:
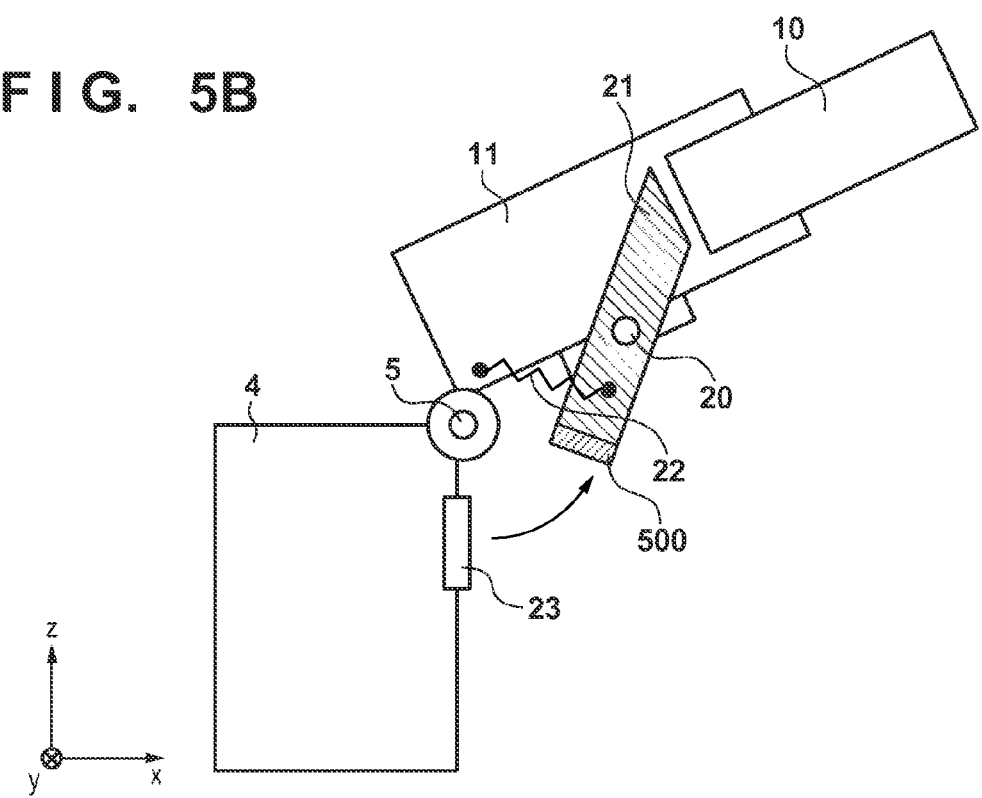

Example 1 will exemplify an arrangement in which a magnet is arranged on a fixing unit. FIGS. 5A and 5B are sectional views of an arm 2 viewed from a lateral direction of a radiation generation apparatus. An arrangement using a ferromagnetic material as a component of the fixing unit will be described with reference to FIGS. 5A and 5B. FIG. 5A shows a state in which the arm 2 in an extended state is closed with respect to a column 4. A restriction unit 21 contacts the column 4 to restrict the opening and closing angle of the arm 2 with respect to the column 4. FIG. 5B shows a state in which the arm 2 is open with respect to the column 4.

In the arrangement shown in FIGS. 5A and 5B, a ferromagnetic material 500 is provided on the contact unit of the restriction unit 21 which contacts the column 4 or near the contact unit. The column 4 is provided with a magnet 23. When the restriction unit 21 contacts the column 4, the ferromagnetic material 500 provided on the restriction unit 21 contacts the magnet 23. This can fix the movement of the arm 2 in the direction to open with respect to the column 4.

Using, as the ferromagnetic material of the restriction unit 21, a magnet different in polarity from the magnet 23 on the column 4 side can fix the movement of the arm 2 in the direction to open. This makes it possible to fix the arm 2 to the column 4 while the restriction unit 21 as a component of the restriction unit controls the opening and closing angle of the extended arm 2. In addition, when the arm 2 is manipulated in the direction to open with respect to the column 4 by applying a force stronger than the magnetic force which fixes the ferromagnetic material 500 of the restriction unit 21 to the magnet 23 of the column 4, the fixation with the magnetic force is released to allow the opening and closing operation of the arm 2.

EXAMPLE 2

Figure 6A:
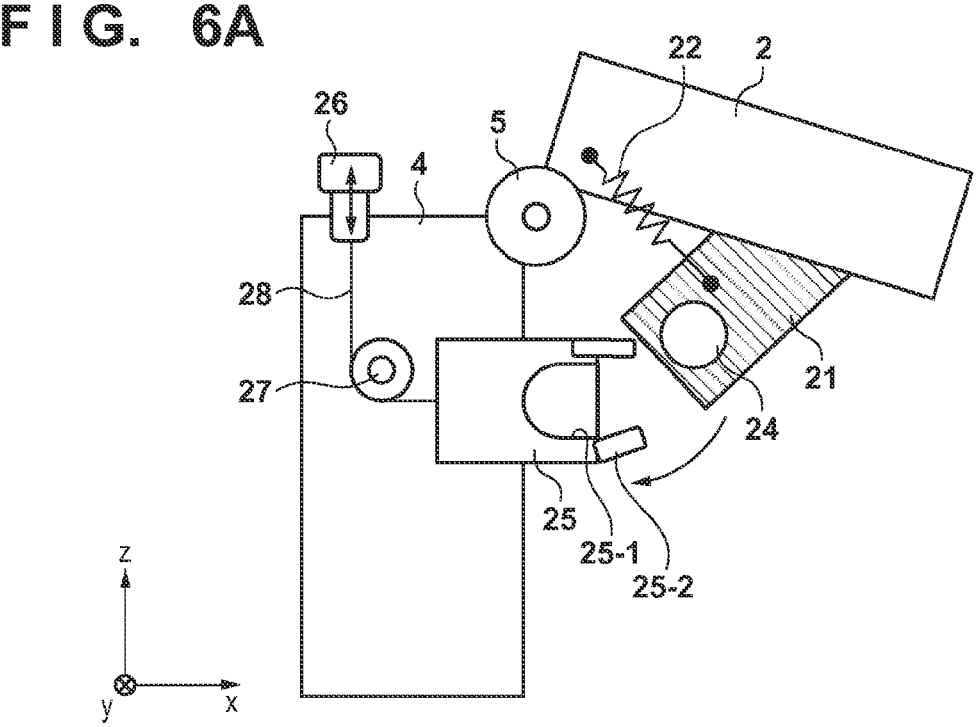
FIGS. 6A and 6B are views showing the arrangement of the radiation generation apparatus according to the second embodiment.
Figure 6B:
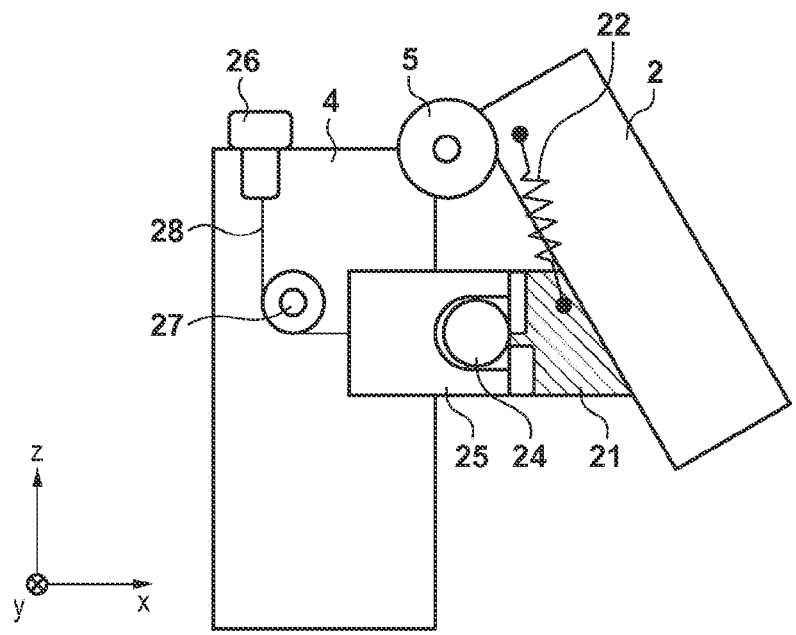

Example 2 will exemplify an arrangement in which a snatch lock and an engaging member which engages with the snatch lock, which constitute a fixing unit, are arranged. FIGS. 6A and 6B are sectional views of an arm 2 viewed from a lateral direction of a radiation generation apparatus. An arrangement using a snatch lock will be described as the arrangement of a fixing unit with reference to FIGS. 6A and 6B.

FIG. 6A shows a state in which the arm 2 is open with respect to a column 4. FIG. 6B shows a state in which the arm 2 in an extended state is closed with respect to the column 4. When a restriction unit 21 contacts the column 4, the opening and closing angle of the arm 2 with respect to the column 4 is restricted.

In the arrangement shown in FIGS. 6A and 6B, the end portion of the restriction unit 21 which contacts the column 4 is provided with an engaging member 24 formed into a cylindrical shape. The column 4 is provided with a snatch lock 25. When the restriction unit 21 contacts the column 4, the engaging member 24 provided on the restriction unit 21 engages with the snatch lock 25 of the column 4, thereby fixing the movement of the arm 2 in the direction to open with respect to the column 4.

More specifically, when the arm 2 in the state shown in FIG. 6A is closed as in the state shown in FIG. 6B, the engaging member 24 is fitted in a groove portion 25-1 of the snatch lock 25.

The inlet portion of the groove portion 25-1 of the snatch lock 25 is provided with a pawl unit 25-2 configured to be rotatable. In addition, a lock operating cam unit (not shown) is provided on the inner circumferential portion of the groove portion 25-1 of the snatch lock 25. As the lock operating cam unit operates, the pawl unit 25-2 performs a rotating operation (a rotating operation from an open state to a closed state; to be also referred to as a closing operation hereinafter). When the engaging member 24 is fitted in the groove portion 25-1, the engaging member 24 causes the lock operating cam unit to operate. The operation of the lock operating cam unit causes the pawl unit 25-2 to perform a rotating operation (closing operation) to close the inlet of the groove portion 25-1, thereby fixing the position of the engaging member 24. With this operation, the engaging member 24 provided on the restriction unit 21 engages with the snatch lock 25 of the column 4, thereby fixing the movement of the arm 2 in the direction to open with respect to the column 4.

The arrangement of a releasing unit for releasing (unlocking) the fixation by the snatch lock 25 will be described next. The radiation generation apparatus further includes a manipulation unit for releasing engagement and a transfer unit for transferring the force input from the manipulation unit to the fixing unit. The fixing unit releases engagement by operating with the transferred force.

In the arrangement shown in FIGS. 6A and 6B, a manipulation unit 26 is provided on the column 4 and configured to be movable in the vertical direction. The snatch lock 25 is provided with a lock releasing cam unit (not shown). As the lock releasing cam unit operates, the pawl unit 25-2 performs a rotating operation (a rotating operation from a closed state to an open state; to be also referred to as an opening operation hereinafter). The lock releasing cam unit is connected to the manipulation unit 26 via a wire 28.

When the lock operating cam unit operates to set the pawl unit 25-2 in a closed state, the lock operating cam unit operates to cause a pull force in the horizontal direction (the right direction in FIG. 6B) to act on the wire 28. This pull force is converted into a downward pull force by a pulley 27 and transferred to the manipulation unit 26. The downward pull force causes the manipulation unit 26 to move downward (FIG. 6B).

When the manipulation unit 26 is pulled upward, the pull force is transferred to a transfer unit (wire 28), and the upward pull force is converted into a pull force in the horizontal direction via the pulley 27 and transferred to the lock releasing cam unit. The lock releasing cam unit operates with the pull force transferred via the transfer unit (wire 28). The operation of the lock releasing cam unit then causes the pawl unit 25-2 to perform a rotating operation (opening operation), thereby opening the inlet of the groove portion 25-1. This allows a manipulation in the direction to open the arm 2 with respect to the column 4.

Note that the arrangement of the fixing unit and releasing unit, which uses the snatch lock, is not limited to the example of the arrangement shown in FIGS. 6A and 6B, and the engaging member 24 and the snatch lock 25 may be respectively provided on the column 4 side and the arm 2 side. In this case, the manipulation unit 26 forming the releasing unit may be provided on the arm 2 side. Providing the manipulation unit 26 on the arm 2 side allows the operator to perform a lock releasing manipulation on the arm 2 side, thereby further improving the maneuverability.

EXAMPLE 3

Figure 7A:
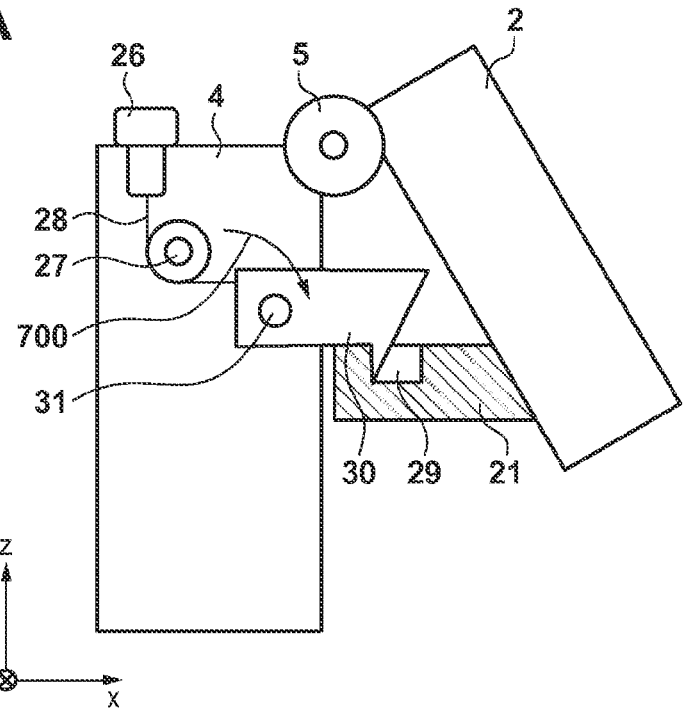
FIGS. 7A and 7B are views showing the arrangement of the radiation generation apparatus according to the second embodiment.
Figure 7B:
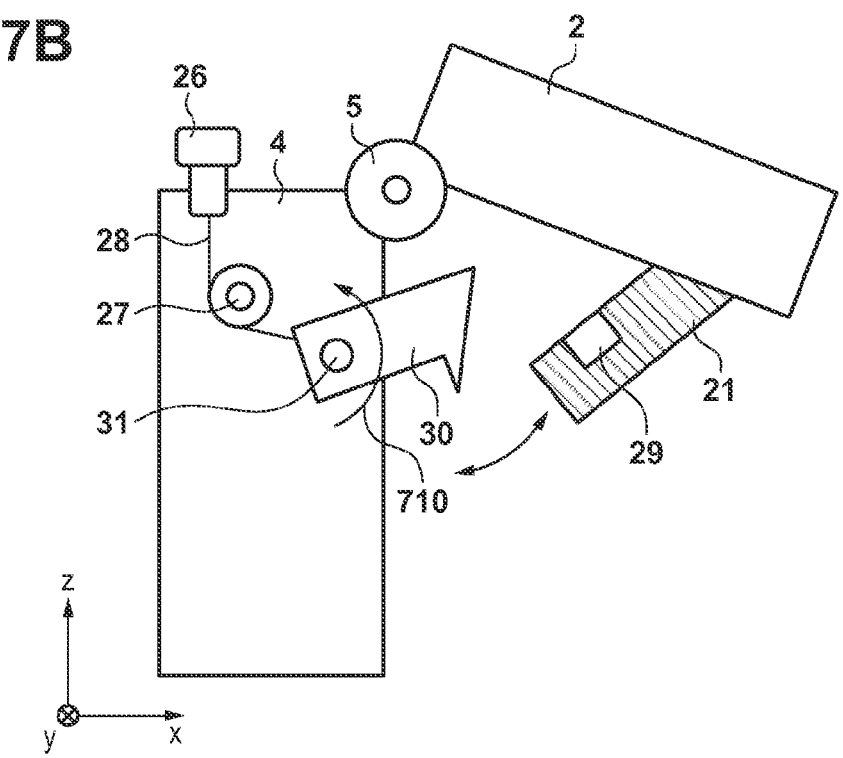

Example 3 will exemplify the arrangement of a fixing unit including a member in which a groove portion (concave portion) is formed and a member on which a convex portion which engages with the groove portion is formed. FIGS. 7A and 7B are sectional views of an arm 2 viewed from a lateral direction of the radiation generation apparatus. In FIGS. 7A and 7B, an arrangement using a restriction unit 21 including a member (pawl unit) on which a convex portion is formed and a groove portion (concave portion) will be described as the arrangement of the fixing unit.

FIG. 7A shows a state in which the arm 2 in an extended state is closed with respect to a column 4. The restriction unit 21 contacts the column 4 to restrict the opening and closing angle of the arm 2 with respect to the column 4. FIG. 7B shows a state in which the arm 2 is closed with respect to the column 4.

In the arrangement shown in FIGS. 7A and 7B, the distal end portion of the restriction unit 21 is provided with a groove portion 29 having a concave shape. The column 4 is provided with a pawl unit 30 which is rotatable about a shaft 31. A convex portion is formed on the distal end portion of the pawl unit 30 which is located on the restriction unit 21 side. When the arm 2 in the state shown in FIG. 7B is closed as in the state shown in FIG. 7A, the convex portion of the pawl unit 30 is fitted in a groove portion 29 of the restriction unit 21.

An inclined portion (tapered portion) is formed on the end portion, of the convex portion of the pawl unit 30, which contacts the restriction unit 21. The length of the arm 2 is variable in accordance with the moving amount of a movable arm 10. The relative angle between a fixed arm 11 and the restriction unit 21 changes in accordance with the moving amount of the movable arm 10. For this reason, the angle of the restriction unit 21 with respect to the pawl unit 30 can also change in accordance with the moving amount of the movable arm 10. Even when such an angle change occurs, since the inclined portion (tapered portion) is formed, the restriction unit 21 can be guided to move along the inclined portion (tapered portion). This makes it possible to cause the pawl unit 30 to smoothly contact the restriction unit 21, thereby making the convex portion of the pawl unit 30 reliably engage with the groove portion 29 of the restriction unit 21.

In the arrangement shown in FIGS. 7A and 7B, a manipulation unit 26 is provided on the column 4 and is configured to be movable in the vertical direction. The pawl unit 30 is connected to the manipulation unit 26 via a transfer unit (a wire 28). When the convex portion of the pawl unit 30 engages with the groove portion 29 of the restriction unit 21, a pull force in the horizontal direction (the right direction in FIG. 7A) acts on the transfer unit (the wire 28) as the pawl unit 30 rotates in the direction of an arrow 700. This pull force is converted into a downward pull force by a pulley 27 and transferred to the manipulation unit 26. The manipulation unit 26 moves downward with the downward pull force (FIG. 7A). By making the convex portion engage with the groove portion 29 in the state shown in FIG. 7A, the movement of the arm 2 in the direction to open with respect to the column 4 can be fixed.

When the manipulation unit 26 is pulled upward, the pull force is transferred to the transfer unit (the wire 28). The upward pull force is converted into a pull force in the horizontal direction (the left direction in FIG. 7B) via the pulley 27 and transferred to the pawl unit 30. The pawl unit 30 rotates in the direction of an arrow 710 with the pull force transferred via the wire 28. The rotating operation of the pawl unit 30 in the direction of the arrow 710 releases the engagement between the convex portion and the groove portion 29. This allows the operator to manipulate the arm 2 in the direction to open with respect to the column 4.

Note that the arrangement of the fixing unit and releasing unit, which uses the convex portion of the pawl unit 30 and the groove portion 29 of the restriction unit 21, is not limited to the example of the arrangement shown in FIGS. 7A and 7B. The groove portion 29 may be provided on the pawl unit 30 on the column 4 side, and the convex portion may be provided on the restriction unit 21 side. In this case, the manipulation unit 26 forming the releasing unit may also be provided on the arm 2 side. Providing the manipulation unit 26 on the arm 2 side makes it possible to perform a lock releasing manipulation on the arm 2 side. This can further improve the maneuverability.

According to this embodiment, while the opening and closing angle of the extended arm 2 is restricted by the restriction unit 21 forming the restriction unit, the arm 2 can be fixed to the column 4. Conventionally, in image capturing during rounds, when image capturing for a patient is complete, the operator retracts the arm 2 to close it with respect to the column 4, and then moves the apparatus. When starting image capturing for the next patient, the operator opens the arm 2 and extends the arm 2 so as to position the radiation generator 1. In contrast to this, since the operator can fix the arm 2 to the column without retracting the arm 2, he/she can move the apparatus while the position of the radiation generator 1 is kept stable.

In addition, it is possible to quickly perform image capturing by releasing the fixation because there is no need to extend the arm 2. This can save the time taken for positioning of the radiation generator 1 by retracting/extending the arm 2, thereby providing a radiation generation apparatus with further improved maneuverability.

(Third Embodiment)

The arrangement of a radiation generation apparatus according to the third embodiment will be described next with reference to FIGS. 8 and 9. The third embodiment will exemplify an arrangement configured to notify the operator when the opening and closing angle of an arm 2 is restricted by a restriction unit 21. The radiation generation apparatus further includes a detection unit 32 which detects contact between a column 4 and the restriction unit 21, a display unit 33 which notifies of the detection result obtained by the detection unit 32, and a control unit 34 which controls display on the display unit 33 in accordance with the detection result obtained by the detection unit 32.

Figure 8:
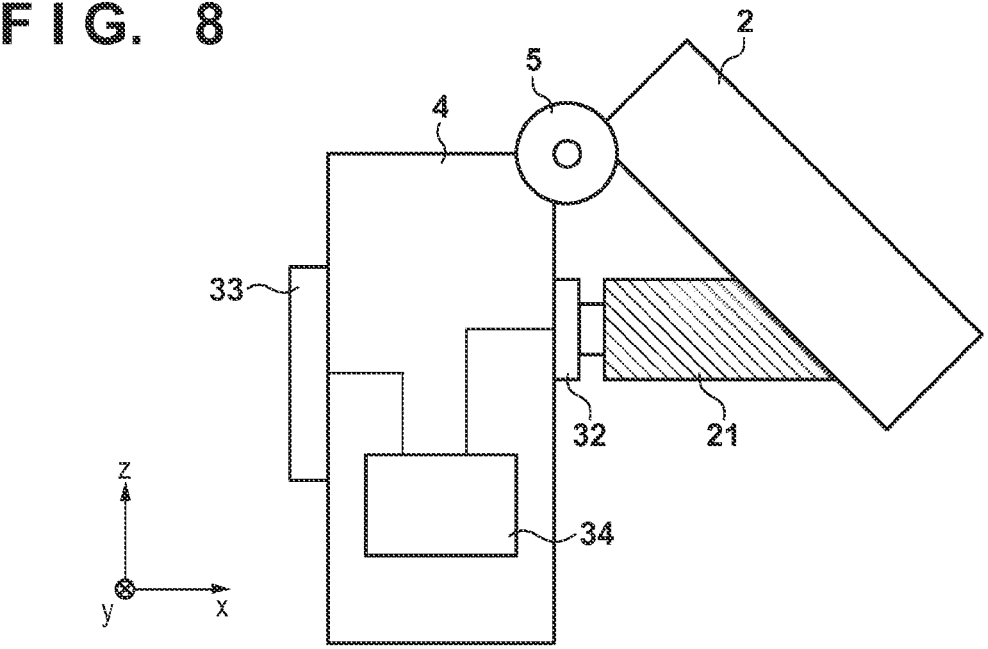
FIG. 8 is a view showing the arrangement of a radiation generation apparatus according to the third embodiment.

FIG. 8 is a sectional view of the arm 2 and the column 4 viewed from a lateral direction of the radiation generation apparatus according to the third embodiment. In the arrangement shown in FIG. 8, the detection unit 32 detects contact between the column 4 and the restriction unit 21. The display unit 33 notifies the operator of the detection result obtained by the detection unit 32. Although the display unit 33 notifies the operator of the detection result obtained by the detection unit 32 by screen display, it is possible to use, instead of this arrangement for notification using screen display, for example, a lamp which notifies the operator with light through vision of the operator or a loudspeaker which notifies the operator by generating a sound. Alternatively, it is possible to use a linear actuator which notifies the operator through tactility by generating vibration. At least one of the arrangements using the display unit 33, a lamp, a loudspeaker, and a linear actuator functions as a notifying unit which notifies the operator of the detection result obtained by the detection unit 32.

The control unit 34 is communicably connected to the detection unit 32 and the display unit 33 wiredly or wirelessly, and controls display on the display unit 33 in accordance with the detection result obtained by the detection unit 32. The control unit 34 can change the display contents of the display unit 33 based on the detection result obtained by the detection unit 32. For example, if the detection result obtained by the detection unit 32 indicates contact, the control unit 34 performs display control to change the display contents of the display unit 33 so as to notify of the contact between the arm 2 and the restriction unit 21. If the detection result obtained by the detection unit 32 indicates non-contact (that contact has been released), the control unit 34 performs display control, in accordance with the detection result obtained by the detection unit 32, to change the display contents of the display unit 33 so as to notify that the contact between the arm 2 and the restriction unit 21 has been released.

Figure 9:
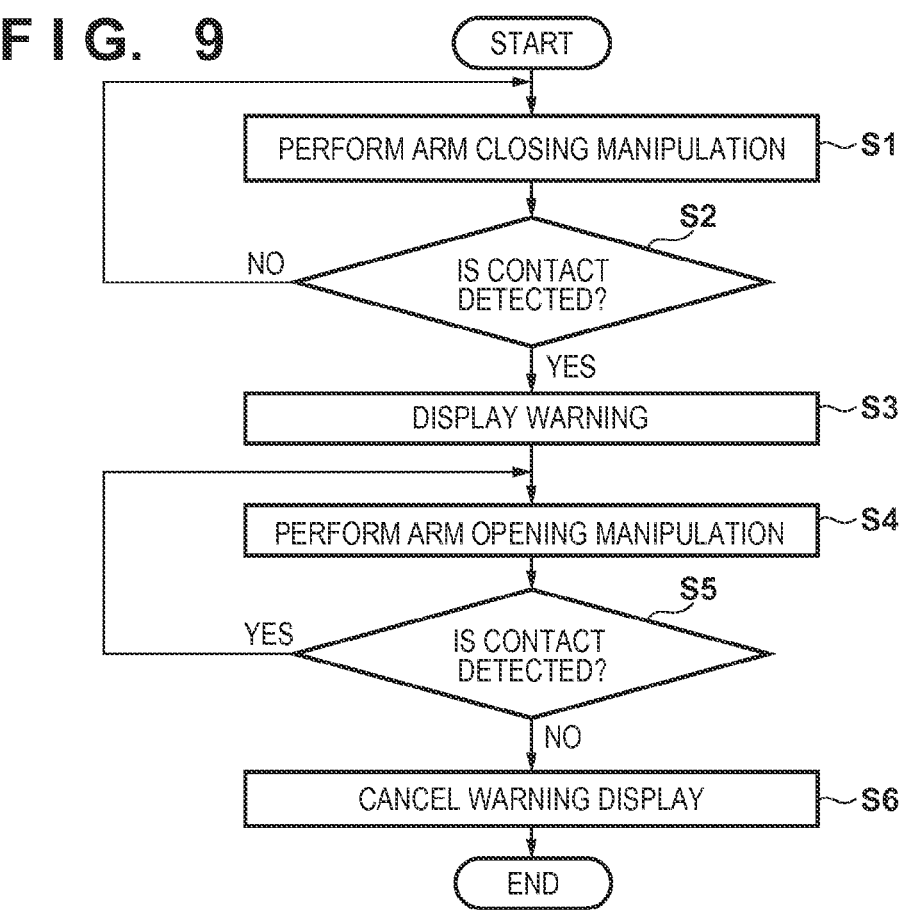
FIG. 9 is a flowchart for explaining processing by the control unit of the radiation generation apparatus according to the third embodiment.

FIG. 9 is a flowchart for explaining a procedure for processing by the control unit 34 when the operator manipulates the arm 2. In step S1, the operator manipulates the arm 2 (closing operation). The operator performs a manipulation to rotate the arm 2 in the direction to close with respect to the column 4 while the arm 2 is extended.

In step S2, the control unit 34 determines whether the detection unit 32 has detected contact between the arm 2 and the restriction unit 21. If no contact is detected (NO in step S2), the process returns to step S1. If the control unit 34 determines in step S2 that contact is detected (YES in step S2), the process advances to step S3.

In step S3, the control unit 34 performs display control to change the display contents of the display unit 33 so as to notify of the contact between the arm 2 and the restriction unit 21 in accordance with the detection result obtained by the detection unit 32. In this case, while the opening and closing angle of the extended arm 2 is restricted by the restriction unit 21 forming the restriction unit, the arm 2 is fixed to the column 4. The control unit 34 performs display control so as to change the display on the display unit 33 from the display contents notifying of non-contact (that contact has been released) to display contents notifying of contact.

In step S4, the operator manipulates the arm 2 (opening manipulation). The operator performs a manipulation to rotate the arm 2 in the direction to open with respect to the column 4 while the arm 2 is extended.

In step S5, the control unit 34 determines whether the detection unit 32 has detected contact between the arm 2 and the restriction unit 21. If contact is detected (YES in step S5), the process returns to step S4. If the control unit 34 determines in step S5 that no contact has been detected (NO in step S5), the process advances to step S6.

In step S6, the control unit 34 performs display control in accordance with the detection result obtained by the detection unit 32 so as to change the display contents of the display unit 33 to notify that the contact between the arm 2 and the restriction unit 21 has been released. The control unit 34 performs display control so as to change the display on the display unit 33 from display contents notifying of contact to display contents notifying of non-contact (that contact has been released).

According to this embodiment, the operator can easily check from notification of whether the opening and closing angle of the arm 2 is in a state to be restricted. Even if, for example, the operator tries to close the arm 2 in an extended state with respect to the column 4, he/she can recognize from notification display that he/she cannot close the arm 2 beyond the angle at which the restriction unit 21 restricts the opening and closing of the arm 2. This reduces the load on the operator in a checking operation concerning restriction on the opening and closing angle of the arm 2 when manipulating the arm 2. This can provide a radiation generation apparatus which further simplifies the manipulation of the arm 2 by the operator and improves maneuverability.

(Fourth Embodiment)

The arrangement of a radiation generation apparatus according to the fourth embodiment will be described next. The radiation generation apparatus according to this embodiment includes a radiation generator 1 which generates radiation, an arm 2 which supports the radiation generator 1, and a column 4 which supports the arm 2. The arm 2 can open and close with respect to the column 4. The fourth embodiment will exemplify a braking unit 50 (FIGS. 10A and 10B) which brakes the arm 2 in accordance with the length of the arm 2 and the opening and closing angle of the arm 2 with respect to the column 4. This embodiment will exemplify a form in which the function of the restriction unit 21 described above is replaced by the braking unit 50. The braking unit 50 (restriction unit 21) according to the embodiment restricts the opening and closing angle of the arm 2 with respect to the column 4 so as to restrict the arm 2 from contacting the floor surface in accordance with the length of the arm 2. That is, the braking unit 50 (restriction unit 21) restricts the opening and closing angle of the arm 2 with respect to the column 4 so as to restrict the radiation generator 1 supported by the arm 2 from contacting the floor surface (ground or horizontal surface) in accordance with the length of the arm 2.

Figure 10A:
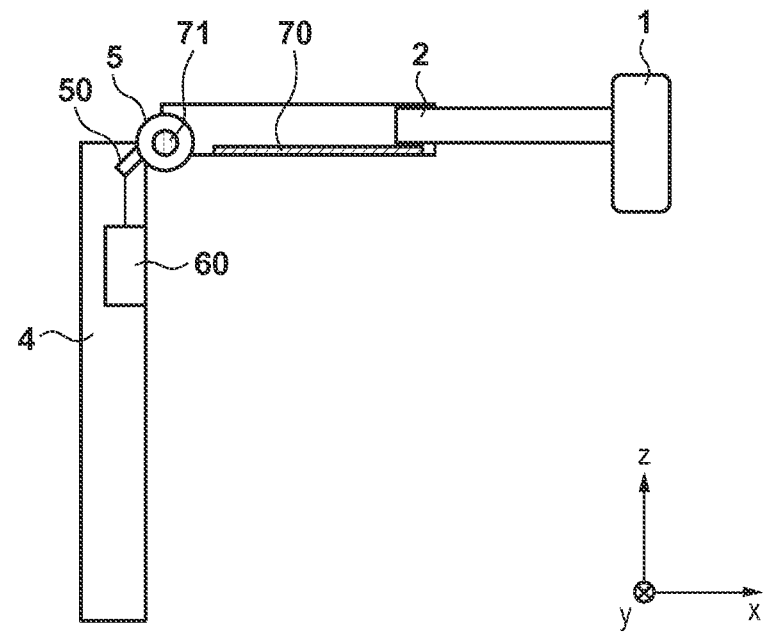
FIGS. 10A and 10B are views for explaining the function of the restriction unit of a radiation generation apparatus according to the fourth embodiment.
Figure 10B:
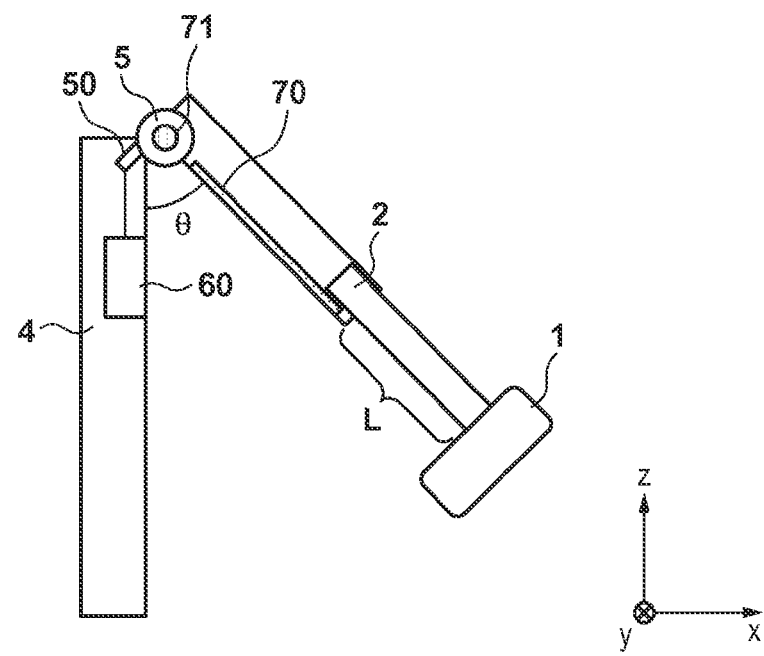

As shown in FIGS. 10A and 10B, a hinge unit 5 is provided between the arm 2 and the column 4. The hinge unit 5 connects the arm 2 to the column 4, and makes the arm 2 open and close with respect to the column 4. The hinge unit 5 includes the braking unit 50 which electrically controls the opening and closing angle of the arm 2. The braking unit 50 has a function of braking the arm 2, that is, a function of braking the rotation motion of the arm 2.

More specifically, the hinge unit 5 includes the braking unit 50 which brakes the arm 2 in the direction to close. The braking unit 50 applies a braking torque to the arm 2 in accordance with the length of the arm 2 and the opening and closing angle of the arm 2 with respect to the column 4. Note that it is possible to properly set braking characteristics by adjusting the magnitude of a current energizing the braking unit 50. As shown in FIG. 10A, a control unit 60 is arranged in the column 4. The control unit 60 controls the magnitude of a current energizing the braking unit 50. The control unit 60 can control the braking characteristics of the braking unit 50 by current control.

Referring to FIG. 10A, an arm length detection unit 70 which detects the length of the arm 2 (moving distance in the translation direction) is provided in the arm 2. The arm length detection unit 70 can be formed by using, for example, a linear scale or laser distance meter. The rotating shaft of the hinge unit 5 is provided with a rotation detection unit 71 which can detect the opening and closing angle of the arm 2 via the rotation of the hinge unit 5.

Figure 11:
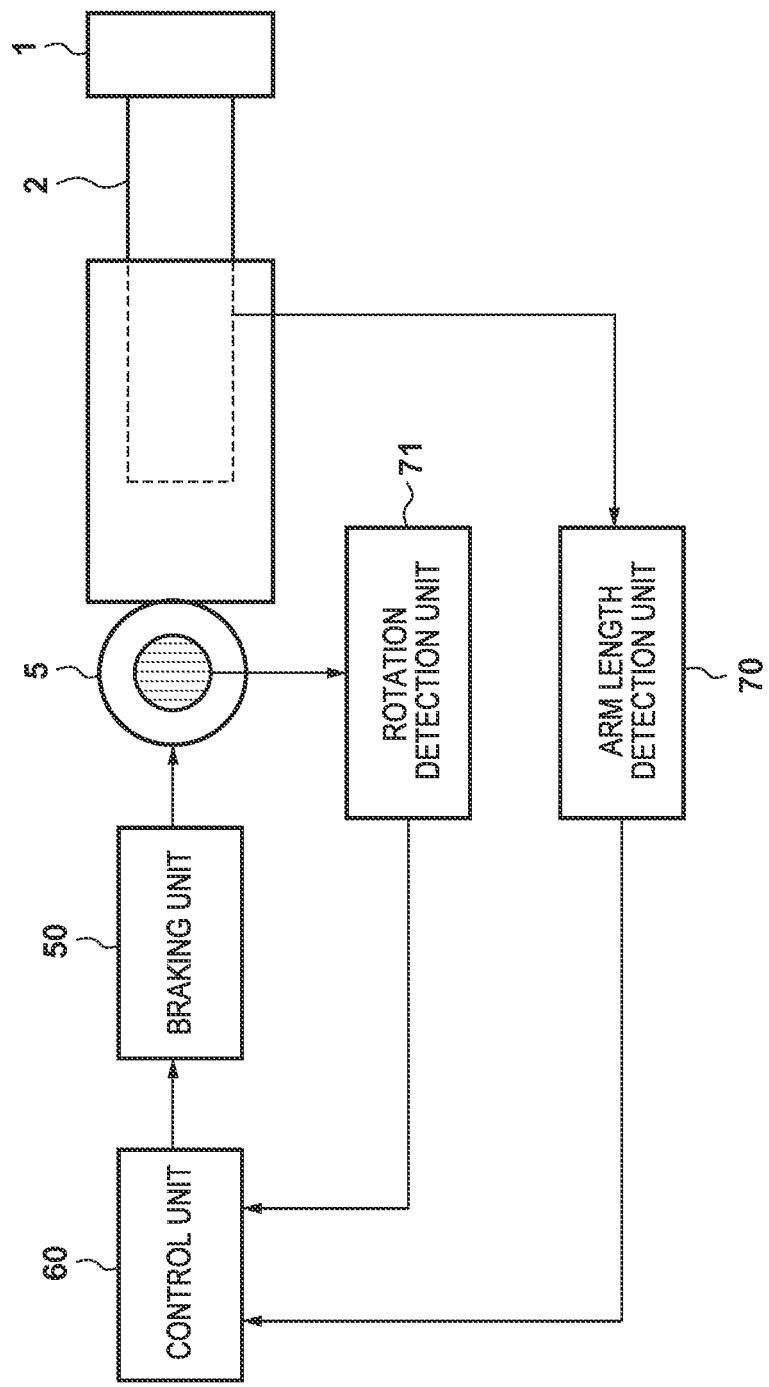
FIG. 11 is a block diagram showing the control arrangement of the radiation generation apparatus according to the fourth embodiment.

FIG. 11 is a block diagram showing a control arrangement according to the fourth embodiment. The arm length detection unit 70 and the rotation detection unit 71 are connected to the control unit 60 arranged in the column 4 via internal wiring such as a flexible cable. The respective detection results obtained by the arm length detection unit 70 and the rotation detection unit 71 are input to the control unit 60. The control unit 60 controls the magnitude of a current energizing the braking unit 50 based on the detection results input from the arm length detection unit 70 and the rotation detection unit 71.

The braking unit 50 brakes the arm 2 by increasing a current energizing the braking unit 50 more than a predetermined threshold in accordance with the length of the arm 2 and the opening and closing angle of the arm 2 with respect to the column 4 under the control of the control unit 60. For example, as shown in FIG. 10B, if the length (L) of the arm 2 is larger than a predetermined value and the opening and closing angle (θ) of the arm 2 is smaller than a predetermined value, the braking unit 50 restricts the opening and closing angle of the arm 2 with respect to the column 4. If the length of the arm 2 is smaller than the predetermined value, the braking unit 50 does not restrict the opening and closing angle of the arm 2 with respect to the column 4. That is, the braking unit 50 releases braking. At this time, the current which energizes the braking unit 50 under the control of the control unit 60 is equal to or less than a predetermined threshold.

According to the arrangement of this embodiment, even if the operator tries to close the arm 2 in an extended state with respect to the column 4, the braking unit 50 brakes the arm 2. This can restrict the opening and closing angle of the arm 2 with respect to the column 4. In addition, controlling the opening and closing angle can ensure a distance for the avoidance of interference such as contact between the radiation generator 1 and the ground (horizontal surface). This makes it possible to provide a radiation generation apparatus which can reduce the load on the operator in returning the length of the arm 2 to a position where no interference occurs and then folding the arm, and can facilitate the manipulation of the arm 2 without any interference with the ground (horizontal surface) and the supporting unit of the apparatus while ensuring a wide range of movement for the radiation generator 1.

This embodiment can provide a radiation generation apparatus which can facilitate the manipulation of the arm without any interference with the ground (horizontal surface).

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-059080, filed Mar. 20, 2014, and Japanese Patent Application No. 2015-003612, filed Jan. 9, 2015 which are hereby incorporated by reference herein in their entirety.

What is claimed is:

1. An x-ray radiation generation apparatus which includes an x-ray radiation generator configured to generate x-ray radiation, an arm configured to support said x-ray radiation generator, said arm having an adjustable length, and a column configured to support said arm, said arm being configured to open and close with respect to said column by changing an angle of said arm with respect to said column, the apparatus comprising
    a restriction unit configured to restrict the angle of said arm based on an adjusted length of said arm.

2. The apparatus according to claim 1, wherein said restriction unit restricts an angle in a direction in which said arm is closed with respect to said column in accordance with the length of said arm.

3. The apparatus according to claim 1, wherein if the length of said arm is longer than a predetermined length, said restriction unit restricts the opening and closing angle of said arm with respect to said column.

4. The apparatus according to claim 1, wherein if the length of said arm is shorter than a predetermined length, said restriction unit releases restriction on the opening and closing angle of said arm with respect to said column.

5. The apparatus according to claim 1, wherein said arm comprises
    a fixed arm supported to be able to open and close with respect to said column, and
    a movable arm held movably with respect to said fixed arm,
    wherein said restriction unit is supported rotatably with respect to said fixed arm and restricts the opening and closing angle by changing a direction with respect to said column in accordance with movement of said movable arm.

6. The apparatus according to claim 5, wherein said movable arm is held to be movable between a retracted position on one end side of said fixed arm and an extended position on the other end side of said fixed arm, and
    wherein said restriction unit restricts the opening and closing angle by changing a direction with respect to said column in accordance with movement of said movable arm from the retracted position to the extended position.

7. The apparatus according to claim 6, wherein one end of said restriction unit is connected to said fixed arm via an elastic member, and
    the other end of said restriction unit contacts said movable arm located at the retracted position, and
    wherein said restriction unit restricts the opening and closing angle by changing a direction with respect to said column by rotation with a force of said elastic member in accordance with movement of said movable arm from the retracted position to the extended position.

8. The apparatus according to claim 7, wherein when said arm moves in a direction to close with respect to said column while said movable arm has moved to the extended position, said restriction unit contacts said column to restrict the opening and closing angle of said arm with respect to said column, and wherein said x-ray radiation generator is held at a position where said x-ray radiation generator does not contact a ground.

9. The apparatus according to claim 7, wherein said restriction unit releases restriction on the opening and closing angle by returning a direction with respect to said column to a direction before the rotation in accordance with movement of said movable arm from the extended position to the retracted position.

10. The apparatus according to claim 9, wherein when said arm moves in a direction to close with respect to said column while said movable arm has moved to the retracted position, said arm is movable without being restricted on the opening and closing angle by said restriction unit, and wherein said x-ray radiation generator is held by said arm at a position where said x-ray radiation generator does not contact a ground.

11. The apparatus according to claim 1, further comprising a fixing unit configured to fix a position of said arm while said restriction unit is in contact with said column.

12. The apparatus according to claim 11, wherein movement of said arm in a direction to open with respect to said column is fixed by fixation by said fixing unit.

13. The apparatus according to claim 11, wherein a magnet is arranged on said fixing unit.

14. The apparatus according to claim 11, wherein a snatch lock and an engaging unit configured to perform engagement with the snatch lock are arranged on said fixing unit.

15. The apparatus according to claim 11, wherein said fixing unit comprises a member in which a groove portion is formed, and
a member on which a convex portion configured to engage with the groove portion is formed.

16. The apparatus according to claim 14, further comprising:

a manipulation unit configured to release the engagement; and
a transfer unit configured to transfer a force input from said manipulation unit to said fixing unit,
wherein said fixing unit operates with the transferred force to release the engagement.

17. The apparatus according to claim 1, wherein said restriction unit comprises a braking unit configured to brake said arm in accordance with a length of said arm and an opening and closing angle of said arm with respect to said column.

18. An x-ray radiation generation apparatus which includes an x-ray radiation generator configured to generate x-ray radiation, an arm configured to support said x-ray radiation generator, said arm having an adjustable length, and a column configured to support said arm, said arm being configured to open and close with respect to said column by changing an angle of said arm with respect to said column, the apparatus comprising a restriction unit configured to restrict the angle of said arm based on an adjusted length of said arm to inhibit said arm from contacting a floor surface.

19. The apparatus according to claim 1, further comprising:

a detection unit configured to detect contact between said column and said restriction unit;
a display unit configured to notify of a detection result obtained by said detection unit; and
a control unit configured to control display on said display unit in accordance with the detection result obtained by said detection unit.

* * * * *